United States Patent [19]

Forbes

[11] Patent Number: 5,187,657
[45] Date of Patent: Feb. 16, 1993

[54] CARDIAC ANALYZER WITH REM SLEEP DETECTION

[75] Inventor: A. Dean Forbes, Palo Alto, Calif.

[73] Assignee: Hewlett-Packard Company, Palo Alto, Calif.

[21] Appl. No.: 505,216

[22] Filed: Apr. 5, 1990

[51] Int. Cl.$^5$ .......................... G06F 15/42; A61B 5/04
[52] U.S. Cl. .......................... 364/413.06; 364/413.05;
  128/670; 128/700; 128/702; 128/731; 128/733
[58] Field of Search ...................... 364/413.03, 413.05,
  364/413.06, 413.01, 413.02; 128/670, 682, 696,
  700, 702, 731, 733

[56] References Cited

U.S. PATENT DOCUMENTS

| 3,807,392 | 4/1974 | Harris | 128/702 |
|---|---|---|---|
| 4,566,463 | 1/1986 | Taniguchi et al. | 128/700 |
| 4,585,011 | 4/1986 | Broughton et al. | 128/733 |
| 4,776,345 | 10/1988 | Cohen et al. | 128/731 |
| 4,794,532 | 12/1988 | Leckband et al. | 364/413.06 |
| 4,796,184 | 1/1989 | Bahr et al. | 364/413.03 |
| 4,836,219 | 6/1989 | Hobson et al. | 128/782 |
| 5,020,540 | 6/1991 | Chamoun | 364/413.06 |
| 5,027,824 | 7/1991 | Dougherty et al. | 128/702 |

FOREIGN PATENT DOCUMENTS 0212278  4/1987  European Pat. Off. ............ 128/682

OTHER PUBLICATIONS

V. Hombach et al., High resolution ECG, Holter ECG monitoring and electrophysiological studies for risk stratification and evaluation of antiarrhythmic therapy. 1989, vol. 2, No. 1/2, 33–35.
Appel et al., Beat to Beat Variability in Cardiovascular Variables: Noise or Music? Nov. 1, 1989; 1139–1148.
Kuchar et al., Noninvasive Recording of Late Potentials: Current State of the Art., Sep. 1989, Pace Bol. 12 pp. 1538–1551.
Farrell et al., Baroreflex Sensitivity and Electrophysiological Correlates in Patients After Acute Myocardial Infarction, Mar. 28, 1990, pp. 945–952.
Advanced Medical Technologies, Monitoring & Diagnostics, Nov. 1, 1987, p. 230.

Primary Examiner—Roy N. Envall, Jr.
Assistant Examiner—Jennifer L. Hazard

[57] ABSTRACT

A compact, cardiac analyzer system provides for monitoring physiological indicators of rapid eye movement (REM) sleep, autonomic fluctuations and ischemia. When any of these "indicators" is detected, a full complement of ECG data is recorded from a subject for subsequent analysis. In the absence of these indicators, only a minimal complement of ECG data is recorded. The system includes a first set of ECG electrode sets, from which the data are recorded only during REM sleep, extreme autonomic drive fluctuations, or ischemia, and a second set of ECG electrode sets, from which the data are constantly recorded. A set of electromagnetic interference sensors is used to assess environmental noise levels so that corrupted data can be rejected or purified. During REM sleep, autonomic drive fluctuations provide a setting for assessing the variability of fractionated potentials in subjects susceptible to sudden cardiac death. In addition, the muscle atonia characterizing REM sleep provides exceedingly low muscle tremor noise levels. Accordingly, cardiac activity is most thoroughly monitored when fluctuating fractionated potentials are most likely to occur and when tremor noise levels are most favorable for their detection. Data recording is minimized in the absence of the indicators, allowing for up to a 5:1 data reduction during a typical sleep cycle.

17 Claims, 3 Drawing Sheets

CARDIAC ANALYZER WITH REM SLEEP DETECTION

BACKGROUND OF THE INVENTION

The present invention relates to medical instruments and, more particularly, to a system and method for detecting fractionated cardiac potentials. A major objective of the present invention is reliable characterization of fractionated cardiac potentials which can be a prodrome of sudden cardiac death.

Sudden cardiac death (SCD) is usually the result of primary electrical instability of the heart. This instability can result when compromised regions of a heart disrupt the electrical signal which activates the heartbeat. These disruptions, while not always fatal, cause fractionated potentials, which provide clues as to a subject's susceptibility to potentially fatal heart problems.

A fundamental challenge in cardiology is to obtain electrocardiograms which are sufficiently free of noise that fractionated potentials can be detected reliably. Being very weak signals, fractionated potentials occurring during electrically active periods of the hearbeat are readily masked by the much stronger cardiac signals. In addition, even when fractionated potentials occur during periods otherwise free of cardiac signals, they can be masked by non-cardiac electrical activity. If the electrical potentials associated with heartbeat activation are precisely registered and carefully processed, information about the fractionated potentials can be recovered reliably. Less careful acquisition and processing can allow the miniscule fractionated potentials to be missed.

Electrocardiograms are usually obtained non-invasively to minimize subject stress and inconvenience, as well as medical expense. Typically, cardiac electrical potentials are detected by electrodes on the body surface connected to an electrocardiograph (ECG) which plots the various potentials as a heartbeat waveform. The cardiac potentials at the electrodes are quite weak, in part, because of current-shunting by tissue between the heart and the skin surface.

The weakness of the monitored cardiac signals makes them vulnerable to noise. The noise can arise from stray electrical fields external to the subject and from noncardiac fields within the subject. Most notably, electrical potentials from the subject's muscular activity and tonicity are superimposed on the cardiac potentials. This superposition makes it more difficult to obtain the accurate heartbeat waveforms required for reliable detection of fractionated potentials.

From an information theory perspective, the problem of accurate representations of electrocardiac activity corresponds to a need to improve the signal-to-noise ratio for the cardiac potentials. Time-averaging is a well-known approach to improving the signal-to-noise ratio for a periodic waveform. When several successive single-cycle waveform segments are aligned and superimposed, the common components reinforce each other while random noise components tend to cancel. This approach has been used often in the detection of abnormal heartbeat patterns (arrhythmias). The arrhythmias can be detected by monitoring a subject over a long interval, making use of a compact, ambulatory ECG such as a Holter recorder.

The fractionated potentials associated with SCD are weaker than the potentials associated with arrhythmias detectable in Holter recordings, and additionally, they can fluctuate. Electrical signals that are shunted around abnormal regions of heart tissue along various routes generate variable electrical potentials at the skin surface. To the extent that the resulting fractionated potentials vary from heartbeat to heartbeat, they will be cancelled rather than enhanced by time-averaging. The achievement of signal-to-noise enhancement by time averaging when prospecting for fractionated potentials is debilitated by the irregularity of the fractionated potentials. In this circumstance, both noise and signal are reduced by time averaging.

Another approach to improving the signal-to-noise ratio of the ECG signals is to minimize the sources of noise. Relaxation techniques and shallow breathing techniques have been used to reduce muscular activity and thus the amount of noise contributed by electrical activity in the muscles. However, the noise reduction provided by these techniques is limited. Furthermore, these techniques require subject relaxation, which may not be achieved or sustained. The requirement of subject relaxation can limit the practical duration over which reliable monitoring can occur.

The duration over which monitoring can occur is important since fractionated potentials occur sporadically in some subjects. Thus, characterization of fractionated potentials can require monitoring a subject over many hours. The length of time required for monitoring a subject introduces another problem: the volume of electrical activity data generated by a subject over such an extended period can make it difficult to identify electrical patterns of interest. Thus, there is a need for some preselection of data to reduce the field of search for the cardiac events of interest.

What is needed is a system and method for detecting fractionated potentials so that a subject's risk of sudden cardiac death can be assessed with greater confidence than previous methods allow. This requires high-precision multichannel electrocardiograms obtained without using time-averaging techniques, which techniques can wash out irregular potentials. Provision for convenient monitoring of a subject over extended time periods is required to enhance the odds that fractionated potentials will be detected, yet the amount of data collected should be limited to an amount which can be practically examined for the fractionated potentials of interest.

SUMMARY OF THE INVENTION

In accordance with the present invention, cardiac electrical potentials are monitored intensively during rapid eye movement (REM) sleep, atypical autonomic nervous system drive, and/or ischemia. In the application of primary interest herein, a cardiac analyzer system includes means for detecting the occurrence of REM sleep or significant departures from average autonomic drive, and an electrocardiograph for monitoring and recording detailed cardiac activity. The REM sleep/autonomic drive detector means can include the ECG electrode sets or dedicated physiological sensors.

The electrocardiograph is coupled to the REM sleep/autonomic drive detector means so that the amount of electrocardiac data recorded is much greater during REM sleep than during other times. Since REM sleep occurs during only about one-fifth of an average sleep cycle, excluding all data outside the REM sleep state permits a 5:1 data reduction, greatly reducing the amount of data to be analyzed for diagnosing SCD potential and similar heart conditions. A computer controller can provide that electrocardiac data be stored only during REM sleep, atypical autonomic drive, and/or ischemia. Alternatively, the computer controller can provide that a limited amount of electrocardiac data be collected at all times, while additional channels of electrocardiac data be recorded only during REM sleep, atypical autonomic drive, and/or ischemia.

A preferred cardiac analyzer system provides for multiple channels of data. These include multiple electrocardiographic channels and can include channels dedicated to the physiological detection of REM sleep states. For example, eye movement sensors, muscle atonia sensors, or brain wave sensors can be used for REM sleep state detection. Multiple electrocardiographic channels are used in parallel to enhance signal-to-noise performance by spatial averaging of received signals. In addition, some channels are dedicated to monitoring environmental noise so that electromagnetic disturbances can be assessed and cancelled from the data channels. A preprocessor provides for baseline correction and spatial averaging for the multiple channels.

REM sleep is characterized by generalized muscle atonia so that noise due to muscular tone is absolutely minimal. REM sleep is also characterized by extreme excursions of both the sympathetic and parasympathetic branches of the autonomic nervous system. Variations in autonomic drive level, in the form of bursts of autonomic nervous system activity, cause rapid heart rate accelerations and decelerations. Individuals susceptible to heart arrhythmias may respond with arrhythmic activity including ectopic beats. Elevated sympathetic stimulation has been shown to correlate with enhanced cardiac electrical instability. Thus, by monitoring subjects during REM sleep, the present invention collects cardiac data both when the events of interest are most likely to occur and when they are least likely to be masked by noise.

The time-varying autonomic drive to the heart has a critical role in inducing cardiac electrical instability. Therefore, cardiac electrical potentials are also analyzed during atypical autonomic drive. Autonomic drive levels can be estimated indirectly by analysis of the electromyographic signals on the electrocardiographic channels. The present cardiac analyzer may supplement the data on the electrocardiogram with data reflective of autonomic nervous system drive obtained from sensors.

Additionally, the ECG data are computer-analyzed to indicate the occurrence of myocardial ischemia, a lack of sufficient blood supply to the heart tissue, which provides another likely interval to observe fractionated potentials. Intense data collection is undertaken during myocardial ischemia.

The present invention provides for a method of characterizing cardiac performance in an individual comprising the steps of attaching a primary set of ECG electrode sets to an individual, optionally attaching dedicated physiological sensors of sleep state and autonomic drive, positioning electromagnetic interference (EMI) sensors near the individual, collecting primary ECG signal data from the electrode sets, sleep state and autonomic drive data from the physiological sensors, and EMI data from the EMI sensors, monitoring the collected data to detect either a REM sleep state, atypical autonomic fluctuations, or ischemia, and, following such detection, initiating recording of the primary ECG signal data and the ancillary physiological signal data.

The multichannel electrocardiograph of the invention has the capability of differentiating nonrepetitive very low amplitude electrical signals in the microvolt range from background noise. This high resolution capability is possible because of the maximum reduction of noise attendant with REM sleep. In addition, the present invention can be implemented as a compact, ambulatory unit which is non-restricting to the patient and thus convenient for usage at home. This is important because unfamiliar environments lead to suppression of REM sleep.

The present invention provides several advantages over the prior systems and methods. Cardiac electrical activity is monitored during a period in which fluctuating fractionated potentials indicative of cardiac electrical instability are most likely to appear. Periods less likely to produce fractionated potentials are excluded, greatly economizing on the amount of data storage required for a diagnosis. The use of spatial averaging of signals enhances the signal-to-noise ratio, and retains the time variations which are lost when time-averaging is used. Channels dedicated to EMI assessment allow data removal or correction for distortions of the electrocardiographic signals of interest. These and other features and advantages of the present invention are apparent from the description below with reference to the following drawings.

DESCRIPTION OF THE PREFERRED EMBODIMENT

Figure 1:
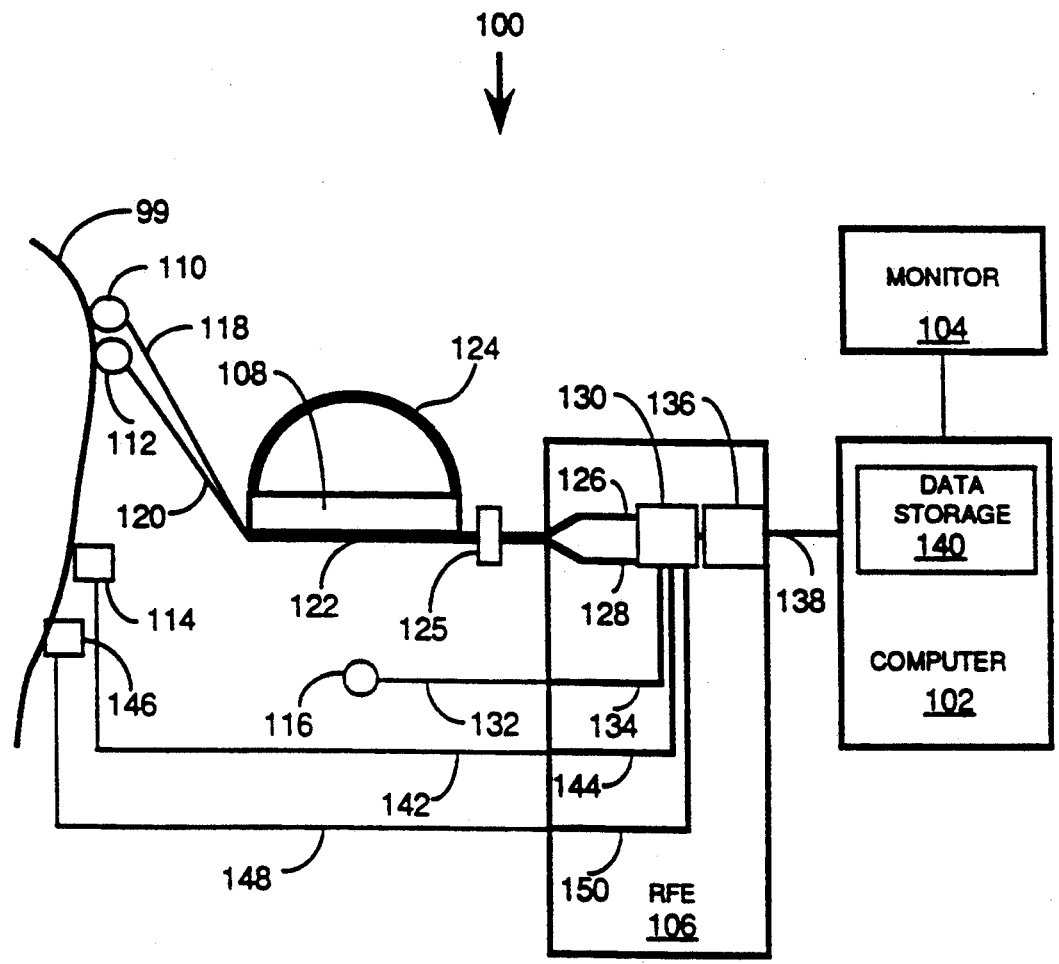
FIG. 1 is a schematic diagram of one embodiment of the cardiac analysis system.

In accordance with the present invention, a cardiac analyzer system 100 for assessing a subject 99 includes a computer 102, a data quality monitor 104, a remote front end (RFE) 106, a cable concentrator unit 108, electrode sets 110 and 112, and auxiliary physiological sensors 114, as shown in FIG. 1. Electrode sets 110 and 112 are attached to subject 99 for monitoring electrocardiographic, electromyographic, and respiratory activity. Sensors 114 are attached to subject 99 for monitoring sleep state. Additionally, electrode sets 110 and sensors 114 are used also to monitor autonomic drive levels. This enables the instrument to correlate fluctuating autonomic nervous system drive mechanisms with fluctuating ECG signals to derive information on fractionated potentials and cardiac electrical stability. In addition, sensors 116 are disposed near subject 99 for monitoring the ambient EMI noise levels. At-subject buffer amplifiers are provided for each ECG electrode set and each EMI sensor.

The signals transduced by electrode sets 110 as well as the dedicated signals provided by sensors 114 are used to detect the existence of REM sleep state. When a REM sleep state is detected by computer 102, data from sensors 114 and 116 and electrode sets 110 and 112 are recorded for off-line analysis. In the absence of a REM sleep state, data from electrode sets 110 and from sensors 114 are not recorded unless fluctuating autonomic drive and/or ischemia are detected. The data from electrode sets 110 and 112 provide multiple channels of electrocardiac data which can be spatially averaged to improve signal-to-noise ratio. Sensors 116 provide environmental noise data which are used to gate out or purify corrupted data. This arrangement results in spatially-averaged low-noise data characterizing the cardiac activity of subject 99 during REM sleep.

More specifically, cardiac electrical signals at the body surface of subject 99 are transmitted via ten primary ECG electrode sets 110 and six secondary electrode sets 112 through ten leads 118 and six leads 120, respectively. Multiple leads 118 and 120 are collected into a manageable cable cluster 122 at concentrator unit 108 that is attached to a belt 124 worn by subject 99. Cable cluster 122 is connected through a quick release connector 125 to RFE 106, a unit positioned near the subject's bed. Furthermore, cable cluster 122 is long enough to permit subject 99 limited ambulation in the vicinity of RFE 106.

Primary ECG electrode sets 110 initiate a first set of data channels 126 and secondary ECG electrode sets 112 initiate a second set of data channels 128. Both sets of channels extend from their respective electrode sets, through RFE 106 to computer 102. RFE 106 includes an analog preprocessor 130 which contains amplifiers, impedance drives/decoders, offset bucking, and common-mode cancellation. Computer 102 implements a multichannel analysis to monitor lead quality, buck out electrode offsets, flag epochs of excessive EMI, form continuously-monitored signals, sense REM sleep, sense autonomic fluctuations, sense ischemia, and control data storage.

EMI from the environment is reduced by shielding subject 99 with a shielding blanket or shielding sleeping bag and by common-mode driving. However, interference that gets through the shielding is sensed by the three EMI sensors 116 which monitor this interference in three dimensions. EMI sensors 116 are placed off subject 99 but in close proximity to ECG electrode sets 110 and 112. The EMI signals are transmitted through leads 132 to RFE 106 and via a third set of data channels 134 to preprocessor 130 where they are amplified and processed along lines paralleling the handling of signals from electrode sets 110 and 112. When extremely noisy intervals occur which corrupt the ECG signals, computer 102 rejects the signals from that interval and halts recording until the EMI abates.

Converter 136 in RFE 106 performs analog to digital conversion, signal interleaving, and computer control execution. The ECG data are formatted by converter 136, are converted to light pulses and are transmitted through fiber optic cables 138 to computer 102. ECG data from the first set of channels 126 are recorded only during intervals of REM sleep or significant autonomic drive variation. Data from the second set of channels 128 are compressed and recorded throughout the monitoring interval. For off-line analysis, all data are recorded on data store 140 capable of storing large amounts of information. The data are optionally displayed on monitor 104, allowing quality-control by the operator.

The use of fiber optic cables 138 and RFE 106, which is battery powered, isolate subject 99 from power line voltages, such as those utilized by computer 102. Additionally, to accommodate hospital requirements, all system elements in contact with subject 99, such as electrodes 110 and 112, leads 118 and 120, concentrator 108, cable cluster 122, and belt 124 are capable of being sterilized.

Detection of REM sleep stage and assessment of autonomic drive status as well as myocardial ischemia are primarily accomplished through analysis of data channels 126 and 128. Additional channels of information are optionally available through sensors 114. Sensors 114 comprise electrodes of an electromyograph and an electro-occulograph, which monitor electrical signals from skeletal and periorbital muscles, respectively. Sensors 114 also comprise electrodes of an electroencephalograph which measures brain activity. Alternatively, other sensors for detecting REM sleep and autonomic nervous system drive levels can be used. Signals from these dedicated sensors are transmitted through sensor leads 142 to the remote front end unit 106. The signals are transmitted over a fourth set of signal channels 144 to preprocessor 130 and then to converter 136. When incoming signals indicate the atonic muscle state and/or rapid eye movements characteristic of REM sleep, the computer 102 initiates recording of the full complement of ECG channels as well as the signals from sensors 116 and 114. By saving full data only during intervals of REM sleep or significant autonomic nervous system drive variation, considerable data reduction is achieved, on the order of 5:1 for overnight monitoring.

Preamplifiers (not shown) are provided for each of the ECG electrodes 110 and 112 and sensors 114 and 116. These preamplifiers are characterized by very high gain, very low noise, wide bandwidth, and wide dynamic range. In addition, the preamplifiers are equipped to determine lead impedances so that poor connections can be corrected and so that respiratory phase can be sensed.

Figure 2:
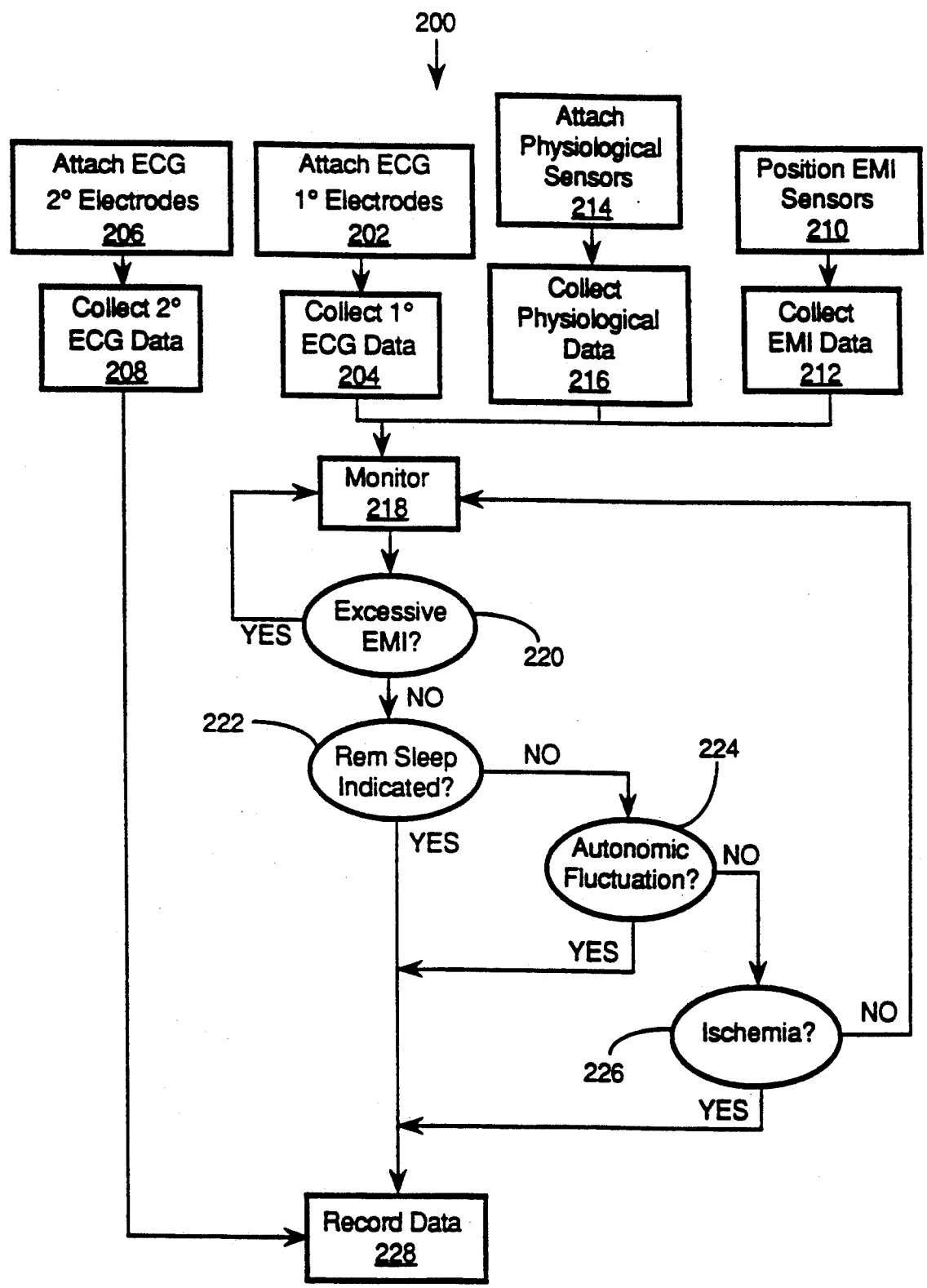
FIG. 2 is a flow chart representing a method of the invention that can be implemented using the cardiac analysis system of FIG. 1.

System 100 is used to implement a method 200, illustrated in FIG. 2. ECG electrode sets 110 are attached, at step 202, to collect, at step 204, a first subset of ECG signal data. ECG electrodes 112 are attached, at step 206, to collect, at step 208, a second subset of ECG data. EMI sensors 116, are positioned, at step 210, to collect, at step 212, EMI data. Subject 99 is optionally fitted, at step 214, with sensors 114 which collect, at step 216, data on physiological indicators of REM sleep and autonomic drive status. Data collected from sensors 114 and 116, and ECG electrode sets 110 are monitored, at step 218. When it is determined, in step 220, that EMI is not excessive, and when there is detected REM sleep, at step 222 (via absence of EMG signals), or autonomic fluctuation at step 224 (via heartrate variability analysis), or ischemia at step 226 (via ST segment analysis), full data are recorded, at step 228. The second subset of ECG data, which is collected, at step 208, from a minimum number of electrodes 112 on a minimum number of signal channels 128, is continuously recorded so that a complete record of ECG activity is available for arrhythmia analysis.

Figure 3:
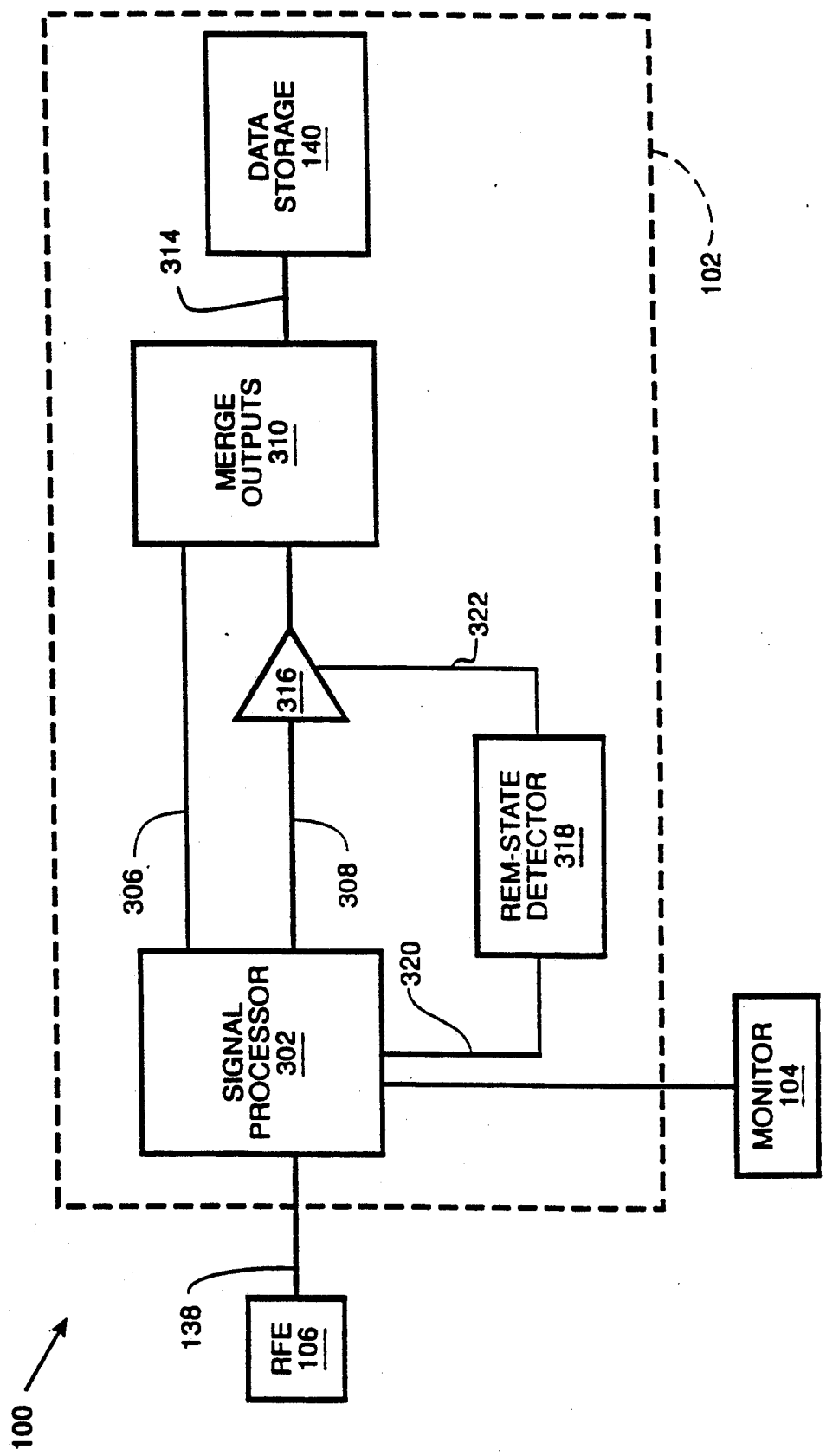
FIG. 3 is a block diagram of the cardiac analysis system of FIG. 1.

Computer 102 comprises a signal processing section 302, which receives data from RFE 106, as shown in FIG. 3. Signal processing section 302 divides the incoming data so that secondary ECG data and other data to be continuously recorded is directed along secondary data path 306 and so that primary ECG data and other data to be selectively recorded are directed along primary path 308. The secondary data along secondary data path 306 are received by interface 310 which forwards the received data to data storage 140 via data path 314.

Primary data line 308 can be selectively enabled and disabled using a gate 316, which. When gate 316 is disabled, no primary data reaches interface 310. When gate 316 is enabled, interface 310 forwards primary data along with secondary data along path 314 for recording by data storage 140. The status of gate 316 is determined by REM-state detector function 318. Detector 318 receives data pertinent to the determination of REM-state, autonomic fluctuations, and inschemia from signal processor 302 via data path 320. Detector 318 analyzes these data to detect the states of interest. Upon detection of REM sleep, autonomic fluctuations or ischemia, detector 318 transmits a control signal along control line 322, enabling gate 316.

In system 100, the ECG data from multiple channels 126 and 128 are combined after analog-to-digital conversion, while an alternative embodiment allows for analog combining of channels prior to conversion to digital form to achieve improved data reduction. Another embodiment of the invention enables the computer 102 to start the recording when incoming data indicate the onset of REM sleep and stop the recording when incoming data indicate the end of REM sleep, while another alternative embodiment has the recording automatically stopped after a set interval of time, on the order of twenty minutes, the typical duration of REM sleep.

Embodiments appropriate for measuring autonomic drive levels allow for off-line spectral analysis of heart rate variability and covariance analysis of heart rate and respiration both performed on data from ECG electrode sets 110. They also allow for off-line analysis of signals provided by sensors 114 which monitor galvanic skin response or respiration. Sensors 114 may measure respiration using impedance plethysmography or strain gauges. Additional sensors 146 may measure blood pressure using cycled arm cuff or servoed finger cuff. Signals from blood pressure sensors 146 would be transmitted through blood pressure leads 148, and blood pressure signal channels 150 to be processed and analyzed. Assessment of baroreflex sensitivity can be realized by co-analyzing spontaneous blood pressure changes and the associated heart rate fluctuation. A decrease in baroreflex sensitivity indicates susceptibility to unstable cardiac activation in response to autonomic drive modulation. Since this insensitivity often appears after myocardial infarction, a cardiac analyzer with capability for measuring blood pressure along with ECG signals is useful for patients who have suffered heart attacks. Alternatively, when sensors 114 measure respiratory rhythms along with ECG during REM sleep, they are useful in detecting sleep apnea or a tendency toward sudden infant death syndrome.

The present invention provides embodiments in which different numbers of ECG electrode sets are used. Any subset or none of the ECG electrode sets can be constantly recorded. Different numbers of EMI electrode sets can be used for data gating, or means for correction can be employed (adaptive noise cancellation). Different numbers and types of sensors can be recorded for off-line analysis. Data can be recorded in analog or digital form and on magnetic paper or other media. These and other variations upon and modifications to the described embodiments are provided for by the present invention, the scope of which is limited only by the following claims.

What is claimed is:

1. A cardiac analyzer comprising:
    data collection means for collecting physiological data from an individual, said data collection means having a data channel set of data channels for transmitting a first data set of said physiological data, said first data set including a first ECG data subset and a sleep state data subset from which a REM sleep state can be detected;
    recording means for recording at least some of said first data set; and
    a computer coupled to said data collection means and to said recording means, said computer having a state detector means to analyze said first data set for indications of said REM sleep state so that said computer causes said recording means to begin recording said first ECG data subset during said REM sleep state.

2. The cardiac analyzer as recited in claim 1 wherein said sleep state data subset is an ECG data subset.

3. The cardiac analyzer as recited in claim 1 wherein said sleep state data subset is measured by at least one element of the set of instruments consisting of an electro-occulograph, an electromyograph, and an electro-encephalograph.

4. The cardiac analyzer as recited in claim 1 wherein said state detector means is further capable of analyzing said first data set for indications of autonomic drive fluctuation so that said computer causes said recording means to begin recording in response to said indications of autonomic drive fluctuation.

5. The cardiac analyzer as recited in claim 1 wherein said state detector means is further capable of analyzing said first data set for indications of ischemia so that said computer causes said recording means to begin recording in response to said indications of ischemia.

6. The cardiac analyzer as recited in claim 1 wherein said data collection means further comprises a second data channel for transmitting a second data set of electrocardiographic data so that said computer causes said recording means to continually record said second data set.

7. The cardiac analyzer as recited in claim 6 wherein said computer causes said recording means to stop recording said first data set when said state detector means indicates that said REM sleep state is no longer present.

8. The cardiac analyzer as recited in claim 6 wherein said computer causes said recording means to stop recording said first data set a fixed period of time after recording of said first data set is begun.

9. The cardiac analyzer as recited in claim 6 wherein said data collection means collects EMI data, said computer having EMI evaluation means for comparing said EMI data to a predetermined EMI threshold, said computer causing said recording means to stop recording said first data set when said predetermined EMI threshold is exceeded.

10. A cardiac analyzer comprising:
    data collection means for collecting physiological data from an individual, said data collection means having at least a first data channel for transmitting a first data set of said physiological data, said first data set including a first ECG data subset and an autonomic drive signal data subset from which autonomic drive fluctuation can be calculated;
    recording means for recording at least some of said first data set; and
    a computer coupled to said data collection means and to said recording means, said computer having a state detector means to analyze said first data set for indications of the autonomic drive fluctuation so that said computer causes said recording means to begin recording said first ECG data subset in response to said indications of the autonomic drive fluctuation.

11. A cardiac analyzer comprising:
data collection means for collecting physiological data from an individual, said data collection means having at least a first data channel for transmitting a first data set of said physiological data, said first data set including a first ECG data subset and an ST waveform data subset from which indications of ischemia can be detected;
recording means for recording at least some of said first data set; and
a computer coupled to said data collection means and to said recording means, said computer having state detector means to analyze said first data set for said indication of ischemia so that said computer causes said recording means to begin recording said first ECG data subset during said indications of ischemia.

12. A method of recognizing a REM sleep state and collecting data characterizing cardiac electrical stability in an individual, said method comprising the steps of:
attaching primary ECG electrode sets to an individual;
collecting primary ECG signal data through said primary ECG electrode sets;
monitoring said primary ECG signal data to determine periods during which a REM sleep state of said individual can be detected; and
initiating recording of said primary signal data when said REM sleep state is detected.

13. The method of recognizing a REM sleep state and collecting data characterizing cardiac electrical stability in an individual as in claim 12 wherein:
said attaching step further comprises attaching secondary ECG electrode sets to said individual;
said collecting step further comprises collecting secondary signal data through said secondary ECG electrode sets; and
said recording step further comprises recording said secondary ECG signal data continuously.

14. The method of recognizing a REM sleep state and collecting data characterizing cardiac electrical stability in an individual as in claim 13 wherein:
said attaching step further comprises attaching physiological sensors to said individual;
said collecting step further comprises collecting physiological signal data through said physiological sensors;
said monitoring step further comprises monitoring said physiological data so the fluctuations of said autonomic drive signal of said individual can be detected and monitoring said primary ECG data so ischemia can be detected; and
said recording step further comprises initiating recording of said primary signal data when the fluctuation of said autonomic drive signal are detected and initiating recording of said primary signal data when ischemia is detected.

15. A method of recognizing autonomic drive fluctuations via heartrate analysis and collecting data characterizing cardiac electrical stability in an individual, said method comprising the steps of:
attaching primary ECG electrode sets to an individual;
collecting primary ECG signal data through said primary ECG electrode sets;
monitoring said primary ECG signal data to determine periods during which autonomic drive fluctuations of said individual can be detected via heartrate analysis; and
initiating recording of said primary signal data when said autonomic drive fluctuations are detected.

16. A method of recognizing periods of ischemia via ST analysis and collecting data characterizing cardiac electrical stability in an individual, said method comprising the steps of:
attaching primary ECG electrode sets to an individual;
collecting primary ECG signal data having ST waveform data through said primary ECG electrode sets;
monitoring said primary ECG signal data to determine periods during which ischmeia in said individual is detected via ST analysis; and
initiating recording of said primary signal data when said ischemia is detected in ST waveform data.

17. A method of characterizing baroreflex sensitivity in an individual as a function of spontaneous fluctuations in blood pressure and heart rate, said method comprising the steps of:
attaching primary ECG electrode sets to an individual;
attaching a non-invasive blood pressure sensor to an individual;
collecting primary ECG signal data through said primary ECG electrode sets;
monitoring said primary ECG signal data and said blood pressure data to determine periods during which heart rate or blood pressure fluctuations occur in said individual; and
initiating recording of said primary ECG signal data and said blood pressure data when said fluctuations occur.

* * * * *